United States Patent [19]

Dahms

[11] Patent Number: 5,603,863
[45] Date of Patent: Feb. 18, 1997

[54] WATER-IN-OIL EMULSIONS

[75] Inventor: Gerd H. Dahms, Velbert, Germany

[73] Assignee: Tioxide Specialties Limited, United Kingdom

[21] Appl. No.: 453,192

[22] Filed: May 30, 1995

Related U.S. Application Data

[62] Division of Ser. No. 24,310, Mar. 1, 1993.

[51] Int. Cl.$^6$ .................. B01J 13/00; A61K 7/42
[52] U.S. Cl. ............... 252/302; 252/314; 424/59; 514/937; 514/938
[58] Field of Search .............. 424/59; 514/938; 252/302, 314

[56] References Cited

U.S. PATENT DOCUMENTS

| | | | |
|---|---|---|---|
| 4,731,242 | 3/1988 | Palinczar | 424/59 |
| 4,820,508 | 4/1989 | Wortzman | 424/59 |
| 4,917,883 | 4/1990 | Strobridge | 424/59 |
| 5,000,937 | 3/1991 | Grollier et al. | 424/47 |
| 5,028,417 | 7/1991 | Bhat et al. | 424/59 |
| 5,041,281 | 8/1991 | Strobridge | 424/59 |
| 5,093,109 | 3/1992 | Mausner | 424/63 |
| 5,169,624 | 12/1992 | Ziegler et al. | 424/59 |
| 5,207,998 | 5/1993 | Robinson et al. | 424/59 |
| 5,208,012 | 5/1993 | Sudo et al. | 514/944 |
| 5,250,289 | 10/1993 | Boothroyd et al. | 424/59 |
| 5,443,759 | 8/1995 | Dahms | 424/59 |

FOREIGN PATENT DOCUMENTS

| | | |
|---|---|---|
| 1602592 | 11/1992 | Australia . |
| 9216026 | 11/1992 | Australia . |
| 0456458 | 11/1991 | European Pat. Off. . |
| 0456460 | 11/1991 | European Pat. Off. . |
| 0456459 | 11/1991 | European Pat. Off. . |
| 49-450 | 1/1974 | Japan . |
| 52-72833 | 6/1977 | Japan . |
| 9124627 | 10/1978 | Japan . |
| 58-43912 | 3/1983 | Japan . |
| 58-62106 | 4/1983 | Japan . |
| 59-62517 | 4/1984 | Japan . |
| 60-149515 | 8/1985 | Japan . |
| 60-149516 | 8/1985 | Japan . |
| 60-149517 | 8/1985 | Japan . |
| 64-030637 | 2/1989 | Japan . |
| 1030637 | 9/1989 | Japan . |
| 5025028 | 2/1993 | Japan . |
| 2217987 | 11/1989 | United Kingdom . |
| 2226018 | 6/1990 | United Kingdom . |
| 2264703 | 9/1993 | United Kingdom . |
| 9006103 | 6/1990 | WIPO . |
| 9009777 | 9/1990 | WIPO . |
| 9011067 | 10/1990 | WIPO . |
| 9217159 | 10/1992 | WIPO . |
| 9307854 | 4/1993 | WIPO . |
| 9311742 | 6/1993 | WIPO . |

*Primary Examiner*—Shelley A. Dodson
*Attorney, Agent, or Firm*—Baker & Botts, L.L.P.

[57] ABSTRACT

The invention concerns a process for producing a water-in-oil emulsion comprising mixing an oil dispersion of particles of a metallic oxide having a primary particle size less than 0.2 micron with one or more emulsifiers and an aqueous phase.

The method enables the production of such emulsions containing relatively small quantities of emulsifiers and a novel emulsion made available by the invention contains less than 1% by weight of emulsifiers, 10 to 60% by weight of an oil phase and at least 40% by weight of an aqueous phase.

The emulsions so formed are useful in preparing UV absorbing compositions such as sunscreens, skin protectants, moisturisers and after-sun lotions.

3 Claims, No Drawings

WATER-IN-OIL EMULSIONS

This application is a division of application Ser. No. 08/024,310, filed Mar. 1, 1993.

This invention relates to water-in-oil emulsions and especially to water-in-oil emulsions containing metallic oxides having a small particle size.

Water-in-oil emulsions containing metallic oxides with a small particle size are known in which the amount of emulsifier present is, typically, 5 to 10% by weight of the emulsion.

It is an object of this invention to provide stable water-in-oil emulsions containing a smaller amount of emulsifier than has been possible hitherto. It is a further object of this invention to provide a convenient process for the production of stable water-in-oil emulsions containing small quantities of emulsifiers.

According to the invention a process for preparing a water-in-oil emulsion comprises mixing a dispersion in an oil of particles of a metallic oxide having an average primary particle size of less than 0.2 micron with one or more emulsifiers and an aqueous phase under conditions in which a water-in-oil emulsion is formed wherein the total amount of emulsifiers present in the water-in-oil emulsion so formed is less than 5 per cent by weight, the particles of metallic oxide comprise from 0.5 per cent to 30 per cent by weight of the emulsion, an oil phase comprises from 10 per cent to 60 per cent by weight of the emulsion and the aqueous phase comprises at least 40 per cent by weight of the emulsion.

Also according to the invention a water-in-oil emulsion comprises 0.5 per cent to 30 per cent by weight with respect to total weight of emulsion of particles of a metallic oxide having an average primary particle size of less than 0.2 micron, said emulsion containing one or more emulsifiers, said one or more emulsifiers being present in an amount of less than 1 per cent by weight with respect to the total weight of emulsion, from 10 to 60 per cent by weight with respect to total weight of emulsion of an oil phase and at least 40 per cent by weight with respect to total weight of emulsion of an aqueous phase.

In preferred embodiments of the process and the product of the invention the metallic oxide comprises an oxide of titanium, zinc or iron.

The average primary particle size of the particles of metallic oxide used in the preparation of the water-in-oil emulsion according to the invention is less than 0.2 micron and where the particles are substantially spherical then this size will be taken to represent the diameter. However, the invention also encompasses particles of metallic oxides which are non-spherical and in such cases the average primary particle size refers to the largest dimension.

Preferably the average primary particle size of the particles is from 0.01 to 0.15 micron and more preferably from 0.01 to 0.06 micron when they are substantially spherical. Particularly useful products are obtained using substantially spherical particles having an average primary particle size between 0.01 and 0.03 micron. For particles having an acicular shape the average largest dimension of the primary particles is preferably less than 0.15 micron and more preferably from 0.02 to 0.10 micron.

When the metallic oxide is titanium dioxide the particles are preferably acicular in shape and have a ratio of largest dimension to shortest dimension of from 8:1 to 2:1.

When the metallic oxide is zinc oxide the particles preferably have an average primary particle size of 0.005 to 0.15 micron and more preferably have an average primary particle size of 0.03 to 0.07 micron.

The particles of metallic oxide may comprise substantially pure metallic oxide but may also carry an inorganic coating or organic coating. For example, particles of titanium dioxide can be coated with oxides of other elements such as oxides of aluminium, silicon or zirconium and a form of acicular, coated titanium dioxide which is especially useful in the products of this invention is disclosed in UK Patent GB 2 205 088.

The particles of metallic oxides may also carry, if desired, a coating of one or more organic materials such as polyols, amines, alkanolamines, polymeric organic silicon compounds, hydrophilic polymers such as polyacrylamide, polyacrylic acid, carboxymethyl cellulose and xanthan gum or surfactants.

Emulsifiers suitable for use in the process of the invention include silicone-based emulsifiers and lipid emulsifiers such as fatty alcohols, fatty acids, glyceryl esters, sorbitan esters, methylglycoside esters and sucrose esters. Many of these emulsifiers are easy to produce from renewable raw materials, are readily bio-degradable and do not contain toxic side products.

In carrying out the process of the invention a dispersion in oil of a metallic oxide having a primary particle size as hereinbefore defined is used. Typically, the dispersion is prepared by milling the metallic oxide in oil in the presence of a particulate grinding medium and in the presence of a dispersing agent.

UK Patent GB 2 206 339 discloses a dispersion in oil of titanium dioxide having an average particle size of from 0.01 to 0.15 micron containing an organic dispersing agent. The dispersions described in GB 2 206 339 are particularly suitable for use in the method of the current invention when it is desired to produce a water-in-oil emulsion containing titanium dioxide.

The technique described in GB 2 206 339 can be used to prepare dispersions in oil of metallic oxides other than titanium dioxide which are suitable for use in the method of the invention.

Suitable dispersing agents which can be used to prepare dispersions of metallic oxides include those disclosed in GB 2 206 339 such as dispersing agents having the formula X.CO.AR in which A is a divalent bridging group, R is a primary, secondary or tertiary amino group or a salt thereof with an acid or a quaternary ammonium salt group and X is the residue of a polyester chain which together with the —CO— group is derived from a hydroxy carboxylic acid of the formula $HOR^1COOH$ in which $R^1$ represents a saturated or unsaturated hydrocarbyl group. Typical dispersing agents are based on ricinoleic acid, hydroxystearic acid and hydrogenated castor oil fatty acid.

Dispersing agents based on one or more polyesters or salts of a hydroxy carboxylic acid or a carboxylic acid free of hydroxy groups can also be used. Other suitable dispersing agents are those monoesters of fatty acid alkanolamides and carboxylic acids and their salts based on $C_6$–$C_{22}$ saturated or unsaturated fatty acids. For example alkanolamides can be based on ethanolamine, propanolamine or aminoethyl ethanolamine. Alternative dispersing agents are those based on polymers or copolymers of acrylic or methacrylic acids, or dispersing agents having ethoxy groups in the constituent radicals such as those based on ethoxylated phosphate esters.

The total quantity of emulsifier used in the process of the current invention is less than 5% by weight of emulsion and preferably less than 1% and suitable emulsifiers are as hereinbefore described. The process of the invention provides a means of producing water-in-oil emulsions containing metal oxide particles using smaller quantities of emulsifiers than has been possible previously. A novel water-in-oil emulsion according to one aspect of the invention contains less than 1% emulsifiers in total.

The composition of the oil phase is chosen to suit the proposed use for the emulsion. For example, when the emulsion is intended for use as a sunscreen the oil phase will generally comprise paraffin oils, triglyceride esters, esters of fatty acids and fatty alcohols or silicone oils.

The water-in-oil emulsions are prepared according to the process of the current invention by mixing an aqueous phase with an oil phase under such conditions that a water-in-oil emulsion is formed.

Typically, the dispersion in oil of metallic oxide is mixed with the emulsifier and, when desired, any other oleophilic components to form the oil phase. This oil phase is subsequently mixed with an aqueous phase to form the water-in-oil emulsion. Alternatively, the dispersion of metallic oxide can be mixed with an emulsion which has previously been prepared by mixing an oil phase containing emulsifier with an aqueous phase.

The emulsions may be prepared at room temperature but it is preferred to use a temperature of at least 40° C. and when components which are solid at room temperature are present it is usually necessary to heat one or both phases before mixing.

Other ingredients can be added to the emulsion depending upon the intended use. These ingredients may be mixed with the emulsion or added to the dispersion, the oil phase or the aqueous phase before these components are mixed together. As examples, perfumes, antioxidants, moisturisers and thickeners are normally added to emulsions which are intended for use as cosmetics.

The water-in-oil emulsions of this invention find use, for example, as sunscreens, as skin protectants, as moisturisers and as after-sun lotions and are particularly useful in preparing products which are transparent to visible light but absorbent to UV light.

The emulsions use smaller quantities of emulsifiers than known emulsions and the emulsifiers which are preferred are easily produced and readily bio-degradable.

The invention is illustrated by the following examples.

EXAMPLE 1

| | Parts by weight |
|---|---|
| 1) Paraffin Oil | 12.5 |
| 2) Dispersion of titanium dioxide in a 1:1 mixture of mineral oil and capric/caprylic triglyceride (sold under the trade name Tioveil MOTG) | 12.5 |
| 3) Sorbitan monooleate (sold under the trade name Span 80) | 0.9 |
| 4) Magnesium sulphate heptahydrate | 0.6 |
| 5) Propylene glycol | 5.0 |
| 6) Demineralised water | to 100 |

Ingredients 1 to 3 were mixed together and heated to 75° C. to form an oil component which was placed in a thermostatted mixing vessel at 75° C. Ingredients 4 to 6 were mixed together and heated to 75° C. to form an aqueous component. The aqueous component was slowly added to the oil component with vigorous stirring (motor-driven paddle stirrer) to form an emulsion. The emulsion was cooled to room temperature over a period of approximately 15 minutes with continuous vigorous stirring. The resulting emulsion was stable for at least four days at 50° C.

EXAMPLE 2

| | % by weight |
|---|---|
| Phase A | |
| PEG-1 Glyceryl Sorbitan Isostearate (Trade Name Arlacel 582) | 3.25 |
| PEG-40 Sorbitan Peroleate (Trade Name Arlatone T) | 0.75 |
| Paraffin Oil | 8.00 |
| Sunflower Oil | 8.00 |
| Caprylic-capric triglyceride (Trade Name Miglyol 812N) | 4.00 |
| Magnesium stearate | 1.00 |
| Dispersion of titanium dioxide in a 1:1 mixture of mineral oil and caprylic/capric triglyceride (Trade Name TIOVEIL MOTG) | 10.00 |
| Phase B | |
| Glycerol | 4.00 |
| Magnesium Sulphate Heptahydrate | 0.70 |
| Demineralised Water | 59.78 |
| 5-Chloro-2-methyl-4-isothiazolin-3-one (and) 2-methyl-4-isothiazolin-3-one (Trade Name Kathon CG) | 0.02 |
| Phase C | |
| Fumed silicon dioxide (Trade Name Aerosil R972) | 0.50 |

Phases A and B were separately heated to 80° C. Phase B was added to Phase A under intensive stirring using a paddle stirrer in a heated vessel. Phase C was added with intensive stirring, and the product was cooled down to 25° C. with stirring at 300 rpm.

EXAMPLE 3

A suncream was prepared as a water-in-oil emulsion according to the following formulation.

| | % by weight |
|---|---|
| Phase A | |
| Laurylmethicone Copolyol (DC Q2-5200[5]) | 0.833 |
| PEG-40 Sorbitan Peroleate (Trade Name Arlatone T[1]) | 0.147 |
| Isohexadecane (Arlamol HD[1]) | 6.00 |
| Sunflower Oil | 6.00 |
| Caprylic-capric Triglyceride (Trade Name Miglyol 812N[4]) | 3.00 |
| Titanium Dioxide dispersion in Mineral Oil and Caprylic-capric Triglyceride (Tioveil MOTG [2]) | 10.00 |
| Phase B | |
| Sodium Chloride | 1.00 |
| Glycerin | 4.00 |
| Allantoin | 0.20 |
| D-Panthenol[3] | 0.80 |
| Demineralised Water | 68.02 |

Suppliers

[1]ICI Specialty Chemicals, [2]Tioxide Specialties Limited, [3]Hoffmann La Roche, [4]Huls, [5]Dow Corning.

Phases A and B were separately heated to 75° C., Phase B was added to Phase A and the two phases were mixed by intensive stirring. The resultant mixture was cooled to 25° C. over 45 minutes whilst the rapid stirring was maintained.

EXAMPLE 4

A suncream was prepared as a water-in-oil emulsion according to the following formulation.

| | % by weight |
|---|---|
| Phase A | |
| Cetyl Dimethicone Copolyol (Abil EM 90[4]) | 0.833 |
| PEG-40 Sorbitan Peroleate (Trade Name Arlatone T[1]) | 0.147 |
| Hydrogenated Castor Oil (Castor Wax) | 0.30 |
| Stearyl Alcohol | 0.10 |
| Magnesium Stearate | 0.20 |
| Mineral Oil | 11.00 |
| Isopropyl Myristate | 4.00 |
| Titanium Dioxide dispersion in Mineral Oil and Caprylic-Capric Triglyceride (Tioveil MOTG[2]) | 10.00 |
| Phase B | |
| Sodium Chloride | 0.80 |
| Magnesium Sulphate Heptahydrate | 0.20 |
| Glycerin | 4.00 |
| Allantoin | 0.20 |
| D-Panthenol[3] | 0.80 |
| Demineralised Water | 67.42 |

Suppliers

[1]ICI Specialty Chemicals, [2]Tioxide Specialties Limited, [3]Hoffmann La Roche, [4]Th Goldschmidt AG.

Phases A and B were separately heated to 75° C. and Phase B was added to Phase A in a heated vessel. The two phases were mixed with a blade stirrer having a circulation speed of 3.115 m/s. After mixing the product was cooled to 25° C. over 45 minutes while the stirring was maintained.

EXAMPLE 5

A sunlotion was prepared as a water-in-oil emulsion according to the following formulation.

| | % by weight |
|---|---|
| Phase A | |
| Laurylmethicone Copolyol (DC Q2-5200 [5]) | 0.833 |
| PEG-40 Sorbitan Peroleate (Trade Name Arlatone T[1]) | 0.147 |
| Sunflower Oil | 14.00 |
| Mineral Oil | 14.00 |
| Caprylic-Capric Triglyceride (Miglyol 812N[4]) | 7.00 |
| Titanium Dioxide dispersion in Mineral Oil and Caprylic-Capric Triglyceride (Tioveil MOTG[2]) | 10.00 |
| Phase B | |
| Sodium Chloride | 1.00 |
| Glycerol | 4.00 |
| Allantoin | 0.20 |
| D-Panthenol[3] | 0.80 |
| Demineralised Water | 48.02 |

Suppliers

[1]ICI Specialty Chemicals, [2]Tioxide Specialties Limited, [3]Hoffmann La Roche, [4]Huls, [5]Dow Corning.

Phases A and B were separately heated to 75° C. and Phase B was added to Phase A in a heated vessel. The two phases were mixed with a blade stirrer having a circulation speed of 3.115 m/s. After mixing the product was cooled to 25° C. over 45 minutes while the stirring was maintained.

EXAMPLE 6

A sunlotion was prepared as a water-in-off emulsion according to the following formulation.

| | % by weight |
|---|---|
| Phase A | |
| Laurylmethicone Copolyol (DC Q2-5200 [5]) | 0.833 |
| PEG-40 Sorbitan Peroleate (Trade Name Arlatone T[1]) | 0.147 |
| Sunflower Oil | 12.80 |
| Mineral Oil | 12.80 |
| Caprylic-Capric Triglyceride (Miglyol 812N[4]) | 6.40 |
| Titanium Dioxide dispersion in Mineral Oil and Caprylic-Capric Triglyceride (Tioveil MOTG[2]) | 10.00 |
| Isoamyl p-Methoxycinnamate (Neo Heliopan Type E 1000[6]) | 3.00 |
| Phase B | |
| Sodium Chloride | 1.00 |
| Glycerol | 4.00 |
| Allantoin | 0.20 |
| D-Panthenol[3] | 0.80 |
| Demineralised Water | 48.02 |

Suppliers

[1]ICI Specialty Chemicals, [2]Tioxide Specialties Limited, [3]Hoffmann La Roche, [4]Huls, [5]Dow Corning, [6]Haarmann & Reimer.

Phases A and B were separately heated to 75° C. and Phase B was added to Phase A in a heated vessel. The two phases were mixed with a blade stirrer having a circulation speed of 3.115 m/s. After mixing the product was cooled to 25° C. over 45 minutes while the stirring was maintained.

I claim:

1. A water-in-oil emulsion comprising 0.5 per cent to 30 per cent by weight with respect to total weight of emulsion of particles of a metallic oxide having an average primary particle size of less than 0.2 micron, said emulsion containing one or more emulsifiers, said one or more emulsifiers being present in a total amount of less than 1 per cent by weight with respect to total weight of emulsion, from 10 to 60 per cent by weight with respect to total weight of emulsion of an oil phase and at least 40 per cent by weight with respect to total weight of emulsion of an aqueous phase.

2. The oil-in-water emulsion of claim 1 wherein the aqueous phase comprises from 40 percent to 90 percent, by weight, of the emulsion.

3. A sunscreen, skin protectant, moisturiser or after-sun lotion comprising a water-in-oil emulsion according to claim 1.

* * * * *

UNITED STATES PATENT AND TRADEMARK OFFICE
CERTIFICATE OF CORRECTION

PATENT NO. : 5,603,863
DATED : February 18, 1997
INVENTOR(S) : Gerd H. DAHMS

It is certified that error appears in the above-indentified patent and that said Letters Patent is hereby corrected as shown below:

Title page, item [30] insert--Feb. 29, 1992 [GB]Great Britain 92 0 4388.4.

Signed and Sealed this

Thirtieth Day of September, 1997

Attest:

BRUCE LEHMAN

Attesting Officer

Commissioner of Patents and Trademarks